United States Patent
Husen et al.

(10) Patent No.: US 8,823,527 B2
(45) Date of Patent: Sep. 2, 2014

(54) CONSCIOUSNESS MONITORING (75) Inventors: Sri Andari Husen, Eindhoven (NL); Bastiaan Feddes, Eindhoven (NL); Thomas Falck, Eindhoven (NL); Constant Paul Marie Jozef Baggen, Eindhoven (NL); Andre Melon Barroso, Eindhoven (NL); Mark Thomas Johnson, Eindhoven (NL); Nicolaas Lambert, Eindhoven (NL); Victor Martinus Gerardus Van Acht, Waalre (NL)

(73) Assignee: Koninklijke Philips N.V., Eindhoven (NL)

( * ) Notice: Subject to any disclaimer, the term of this patent is extended or adjusted under 35 U.S.C. 154(b) by 191 days.

(21) Appl. No.: 13/390,520

(22) PCT Filed: Aug. 25, 2010

(86) PCT No.: PCT/IB2010/053817
§ 371 (c)(1),
(2), (4) Date: Feb. 15, 2012

(87) PCT Pub. No.: WO2011/027263
PCT Pub. Date: Mar. 10, 2011

(65) Prior Publication Data
US 2012/0161969 A1 Jun. 28, 2012

(30) Foreign Application Priority Data
Sep. 3, 2009 (EP) .................................. 09169337

(51) Int. Cl.
*G08B 23/00* (2006.01)

(52) U.S. Cl.
USPC .................. 340/573.1; 340/576; 600/544

(58) Field of Classification Search
USPC .............. 340/573.1, 575, 576; 600/544, 545; 607/108
See application file for complete search history.

(56) References Cited

U.S. PATENT DOCUMENTS

| | | | |
|---|---|---|---|
| 5,846,206 A | 12/1998 | Bader | |
| 6,167,298 A | 12/2000 | Levin | |
| 6,416,480 B1 | 7/2002 | Nenov | |
| 6,756,903 B2 * | 6/2004 | Omry et al. | 340/576 |
| 6,993,380 B1 * | 1/2006 | Modarres | 600/544 |
| 7,137,992 B2 * | 11/2006 | Zhang | 607/104 |
| 7,403,815 B2 * | 7/2008 | Katz et al. | 600/544 |
| 7,654,948 B2 * | 2/2010 | Kaplan et al. | 600/26 |
| 8,103,328 B2 * | 1/2012 | Turner et al. | 600/544 |
| 8,199,018 B2 * | 6/2012 | Shigetou | 340/573.1 |
| 8,391,967 B2 * | 3/2013 | Freer et al. | 600/544 |
| 2007/0055114 A1 | 3/2007 | Viertio-Oja et al. | |
| 2007/0179399 A1 | 8/2007 | Viertio-Oja et al. | |

FOREIGN PATENT DOCUMENTS

GB    2334127 A    8/1999

* cited by examiner

Primary Examiner — John A Tweel, Jr.

(57) ABSTRACT

A method for automatically monitoring consciousness of a person and triggering an alarm if the monitored person is not in a state of full consciousness is provided. The method comprises the steps: monitoring at least one aspect of the behavior of the person (S1); analyzing whether the monitored behavior of the person corresponds to an expected behavior for a state of full consciousness or not (S2, S2'); triggering an alarm if the analysis results in that the detected behavior does not correspond to the expected behavior (S3).

20 Claims, 3 Drawing Sheets

CONSCIOUSNESS MONITORING

FIELD OF INVENTION

The present invention relates to automatic consciousness monitoring. More specifically, the present invention relates to a method for automatically monitoring consciousness of a person and triggering an alarm if the monitored person is not in a state of full consciousness and to a monitoring and alarming device for automatically monitoring consciousness of a person and outputting an alarm if the monitored person is not in a state of full consciousness.

BACKGROUND OF THE INVENTION

In modern hospitals, there is a trend towards implementation of so-called rapid response systems. A rapid response system identifies deteriorating patients in general wards before the deterioration has become too profound. Upon detection of a deteriorating patient, the respective patient is assessed by a rapid response team to prevent further deterioration, admission to the intensive care unit (ICU), and even death.

Since early deterioration of patients can be observed from changes in the patient's vital signs, it becomes more and more common that vital signs of patients in general wards of hospitals are monitored such that a rapid response team can intervene rapidly when deteriorations are detected. In this way adverse outcomes can be prevented. While the four vital signs heart rate, blood pressure, respiration rate, and temperature can be automatically measured and monitored by means of well known medical sensors, the level of consciousness being a fifth vital sign has commonly to be determined manually by care personnel. It should be noted that the respiration rate is considered the most important parameter and the level of consciousness is considered the second most important parameter for detecting a decline in patient condition in hospitals.

In this context, the term consciousness means the ability of an individual to respond appropriately to environmental stimuli. Loss of this ability is generally judged as an alteration of consciousness. There are two major aspects of consciousness: on the one hand arousability, namely whether the individual responds to external stimuli, and on the other hand the appropriateness of the content of the consciousness, namely whether the response to stimuli, in particular stimuli requiring contextual response (such as for instance the answer to the question "What is your name"), is within the appropriate context.

Conventionally, the level of consciousness of patients is assessed by doctors, nurses, or other health care professional in terms of the responsiveness to the environment. Various methods and scales have been developed to assess and quantify the level of consciousness. The Glasgow Coma Scale (GCS) is the most widely used scoring system in quantifying the level of consciousness of patients following traumatic brain injury. The GCS quantifies the verbal, motor, and eye-opening responses to verbal and pain stimulation separately. Each type of response is scored, on the scale of 1 to 4, 1 to 5, and 1 to 6, respectively, depending on the type of responses. A lower score means a more decreased level of consciousness. The scores of each response are added into a final score on a scale of 3-15.

Further, the so-called AVPU scale which is a simplification of the GCS scale is also commonly used. In the AVPU scale there are only four possible outcomes which are assessed from the best eye, voice, and movement responses to the stimuli. According to this scale, "Alert" signifies a state in which the patient is fully awake, shows spontaneous eye opening, responds to voice, and has bodily motor function; "Voice" signifies a state in which the patient is not fully awake but responds to the assessor's voice; "Pain" signifies a state in which the patient does not respond to voice but responds to a painful stimulus administered, such as a fingernail press by the assessor; and "Unconscious" signifies a state in which the patient does not respond to pain. According to the AVPU scale the first characters "A", "V", "P", and "U" of the states are also used as abbreviations for the respective states. In clinical practice, the AVPU scale is commonly used for rapid assessment of acutely ill patients. Further, because it is a simpler tool as compared to the GCS scale, it has also been incorporated into many early warning score systems.

The assessment of consciousness according to the above described methods is based on a fairly subjective manual task and is commonly performed in hospitals in periodic spot check manner, typically every 8 hours.

As has been pointed out above, there is a demand for automated consciousness detection.

U.S. Pat. No. 6,416,480 B1 describes a system and a method for computerized automated acquisition of the Glasgow Coma Score (GCS) for quantifying the level of consciousness following traumatic brain injury. The system is intended to be used in medical units such as intensive care units, emergency rooms, and operating rooms. The assessment of critically ill patients is performed on a periodic basis based on stimulus-induced standard physiological and verbal responses of the patient. The system aims at providing a coma score which corresponds one-to-one with the GCS as obtained by human assessors. Such an automated system comprises the following advantages: (1) it does not introduce a subjective bias based upon previous assessments, as may commonly occur when nurses and physicians assess the GCS; (2) it eliminates the errors often made by the nurses or physicians while recording the GCS on paper or entering it into a computerized system by hand; (3) it may offer significant savings in personnel costs at the hospital intensive care units, emergency rooms, neurology/neuroscience wards and other sites where the level of consciousness of patients needs to be evaluated at regular intervals; (4) it permits more frequent assessment and thus a more rapid response to changes in the patient's status, thereby potentially saving lives as well as decreasing or preventing brain damage. However, the described system also comprises some disadvantages, namely: In every cycle of the GCS assessment, at least two verbal stimulations are necessary for assessing the highest scores of verbal and motor response. The frequent GCS assessments will potentially annoy the patients which may lead to patients ignoring the stimulation. However, since ignoring the stimulation may lead to even more unpleasant stimulation (pain stimulation), the patient may consequently try to remove the stimulators altogether. Further, in order to achieve the GCS results, the described system exploits measurement and detection methods which are invasive and impractical for applications in general wards.

Although in some cases a detailed assessment of the level of consciousness is required which legitimates a detailed analysis involving high costs and discomfort for the patient, there is a demand for an easy way of answering the question whether a patient is in state of full consciousness or not. In particular, there is a demand for an automatic procedure and system for monitoring consciousness of patients in general wards of hospitals (i.e. not in the intensive care unit (ICU) or in the emergency room (ER)). Further, it has been found that periodic and deliberate stimulations are potentially annoying and uncomfortable to the patients. Such annoyance can result in non-compliance behavior of the patients.

SUMMARY OF THE INVENTION

It is an object of the present invention to provide a method and device with which automatic surveillance of the consciousness of persons in general wards of hospitals is enabled without requiring procedures which are invasive and/or annoying for the monitored persons.

This object is solved by a method for automatically monitoring consciousness of a person and triggering an alarm if the monitored person is not in a state of full consciousness. The method comprises the steps: monitoring at least one aspect of the behavior of the person; analyzing whether the monitored behavior of the person corresponds to an expected behavior for a state of full consciousness or not; triggering an alarm if the analysis results in that the detected behavior does not correspond to the expected behavior. Thus, the at least one aspect of the behavior of the person is monitored. The monitored aspect of behavior can for instance be movement of a body part and its pattern, change in posture, eye movement, speech (conversation/voice production), input to an input device, amount of interaction with devices in the person's vicinity or another intentional action of the person. These aspects of the behavior of the person can be exclusively monitored in a non-invasive way and without providing discomfort to the person or disturbing the person. Preferably monitoring is realized non-invasively. In this context, the term "state of full consciousness" means the "alert" level on the AVPU scale (Alert, Voice, Pain, Unconscious). Further, it is only analyzed whether the person is in the state of full consciousness or not and no prediction as to further sub-states is made. In the case that the automatic assessment leads to the result that the person is not in the state of full consciousness, an alarm is triggered such that the consciousness of the person can be manually assessed in a more detailed manner, e.g. according to the GCS or AVPU scale if deemed necessary. As a consequence, a method is provided which is suited for monitoring consciousness of patients e.g. in general wards of a hospital since it does not require invasive methods to distinguish between a state of full consciousness and a single further state of reduced consciousness. The level of full consciousness can be easily determined through monitoring the behavior of the person and the responsiveness of the person to naturally occurring environmental stimuli, in particular environmental acoustics stimuli. Persons being in the state of full consciousness show a more active behavior as compared to persons of reduced consciousness. Further, they will be more sensitive to the environmental stimuli and will respond faster. In particular, the level of full consciousness can easily be inferred from characterizing occurring environmental stimuli and the person's response thereto.

Preferably, the step of analyzing is performed to discern between exactly two states, namely a state of full consciousness and a state corresponding to not full consciousness. For monitoring persons, e.g. in general wards of hospitals, such an assessment is sufficient. If a more detailed analysis of the severity of "not full consciousness" becomes necessary, this can be done manually after the alarm has been triggered. Further, the analysis whether the person is in the state of full consciousness or not can be made without subjecting the person to discomfort and even without subjecting the person to deliberate stimulations. The method does not provide an analysis according to a full consciousness scale but only reliably predicts whether a person is in a safe state of full consciousness or not. According to one aspect, the method comprises detecting the response in the monitored behavior of the person to at least one stimulus. Preferably, according to one aspect, the at least one stimulus is a naturally occurring environmental stimulus such as an environmental acoustic stimulus (and not an intentionally provided artificial stimulus), since this has the advantage that possible annoyance of the person which may occur with respect to intentional artificial stimuli applied in regular intervals can be prevented. To this end, the naturally occurring environmental stimulus can also be detected, e.g. by means of a microphone in the case of acoustic stimuli. After such a stimulus has been detected, the response of the person to the stimulus is monitored. Thus, it is assessed whether the person is in a state of full consciousness or not through automatically monitoring the behavior of the person and the responsiveness of the person to the environmental stimuli.

Thus, preferably, the method comprises detecting at least one environmental stimulus and monitoring whether the monitored behavior shows a response to the at least one environmental stimulus. According to one aspect, the person is not subjected to artificial intentional stimuli.

According to another aspect, the person is subjected to at least one artificial intentional stimulus and the response of the person to the at least one intentional stimulus is measured. Preferably, the intentional stimulus is provided in a non-invasive manner. For example, the intentional stimulus can be provided by a buzzer, in form of vibration or sound, as light signal, or in form of a challenge or puzzle presented to the person in response to which an answer has to be entered via an input device, and the like. For example, the person can be subjected to the intentional stimulus in intervals between 30 minutes and 4 hours, preferably in intervals between 1 hour and 2 hours.

Preferably, the response times of responses to subsequent stimuli are analyzed and tracked over time. It has been found that a negative trend in response times can provide additional health condition information.

According to a particularly preferred realization, the person is subjected to an intentional stimulus only if the analysis based on the person's behavior and the person's response has led to the conclusion that it is likely that the person is not in a state of full consciousness. In this case, providing the intentional stimulus and monitoring the person's response is only used to verify the result from the analysis based on the person's behavior and response to naturally occurring environmental stimuli. In this way, annoyance and non-compliance of persons which may result from frequent intentional stimuli can be prevented. Thus, preferably the person is subjected to an artificial intentional stimulus if the monitored behavior of the person does not correspond to an expected behavior for a state of full consciousness.

The object is also solved by a monitoring and alarming device for automatically monitoring consciousness of a person and outputting an alarm if the monitored person is not in a state of full consciousness. The device comprises: at least one sensor adapted for sensing at least one aspect of the behavior of a person; and a processing unit adapted for monitoring a signal from the at least one sensor and adapted to judge from the sensed behavior whether the person is in a state of full consciousness or not; the processing unit being adapted to trigger an alarm if it is judged that the monitored person is not in the state of full consciousness. Thus, the at least one aspect of the behavior of the person is sensed by the sensor and the sensor signal is monitored. The thus-monitored aspect of behavior can for instance be a movement of a body part and its pattern, a change in posture, eye movement, speech (conversation/voice production), person input to an input device, and the amount of interaction with devices in the person's vicinity or another intentional action of the person. These aspects of the behavior of the person can be exclusively monitored in a non-invasive way and without providing discomfort to the person or disturbing the person. The at least one sensor can e.g. be formed by one or more motion sensors such as 1-D, 2-D, or 3-D accelerometers to be attached to a person being monitored, by one or more pressure sensors attachable to a person's bed, a video camera for monitoring eye movements or other movements, one or more microphones for detecting acoustic signals, controls of personal entertainment devices, one or more personal light switches, a personal telephone unit, and other devices/controls in the person's vicinity. For example, the at least one sensor can be also be formed by a combination of several sensors of the same or different types. In the case that the automatic assessment leads to the result that the person is not in the state of full consciousness, the processing unit triggers an alarm such that the consciousness of the person can be manually assessed in a more detailed manner. As a consequence, a device is provided which is suited for monitoring consciousness of persons e.g. in general wards of a hospital since it does not require invasive methods to distinguish between a state of full consciousness and a single further state of reduced consciousness.

Preferably, the processing unit is adapted to discern between exactly two states, namely a state of full consciousness and a state corresponding to not full consciousness. For monitoring persons e.g. in general wards of hospitals such an assessment is sufficient. If a more detailed analysis of the severity of "not full consciousness" becomes necessary, this can be done manually after the alarm has been triggered. Further, the analysis whether the person is in the state of full consciousness or not can be made without subjecting the person to discomfort and even without subjecting the person to deliberate stimulations. Thus, the device reliably predicts whether a person is in a safe state of full consciousness or not.

According to one aspect, the device comprises at least one stimulation device adapted for providing an artificial intentional stimulus to the person being monitored. In this case, the monitoring and alarming device can actively subject the person to a stimulus and detect the person's response. The stimulation device can e.g. formed by a sound and/or vibration generating device such as e.g. a loud speaker or buzzer, by a light signal generating device, by a tactile information generating device such as a vibration and/or movement generator, and/or by a more complex device such as a person interface device comprising a display, and the like.

Preferably, the monitoring and alarming device comprises a detection unit for detecting at least one environmental stimulus and the processing unit is adapted for analyzing whether the monitored behavior shows a response to the at least one environmental stimulus.

In this case, the monitoring and alarming device is capable of identifying environmental stimuli and monitoring if the person shows an appropriate response. Thus, it is not necessary to regularly subject the person to intentional stimuli and the problem of possible annoyance of the person which may occur with respect to intentional artificial stimuli applied in regular intervals can be prevented. For example, the detection unit can be formed by one or more microphones for detecting acoustic stimuli.

Preferably, the processing unit is adapted to provide an artificial intentional stimulus to the person and analyze whether the person shows a response to the artificial intentional stimulus in the sensed behavior when it has been judged that the person is not in the state of full consciousness. In this case, the consciousness of the person can be reliably monitored in a manner which is comfortable for the person by only monitoring the person's behavior and responses to environmental stimuli as long as this results in a finding of "not fully conscious". Further, if a deviation from the state of full consciousness is found based on these parameters, the intentional stimulus can be provided to verify the result. This results in that, on the one hand, possible annoyance and non-compliance of persons can be prevented and, on the other hand, unnecessary alarms can be prevented due to the achieved redundancy.

Preferably, the at least one sensor comprises at least one motion sensor. In this case, sensing of at least one aspect of the behavior of a person can be achieved in a cost-efficient manner which is easy to implement. Preferably, the device comprises a patient unit adapted to be attached to the person comprising the at least one motion detector and a stimulation device. In this way, reliable consciousness monitoring is achieved with a compact and cost-efficient device.

BRIEF DESCRIPTION OF THE DRAWINGS

Further features and advantages of the present invention will arise from the detailed description of embodiments with reference to the enclosed drawings.

DETAILED DESCRIPTION OF EMBODIMENTS

Embodiments of the present invention will now be described with reference to the Figures.

Figure 1:
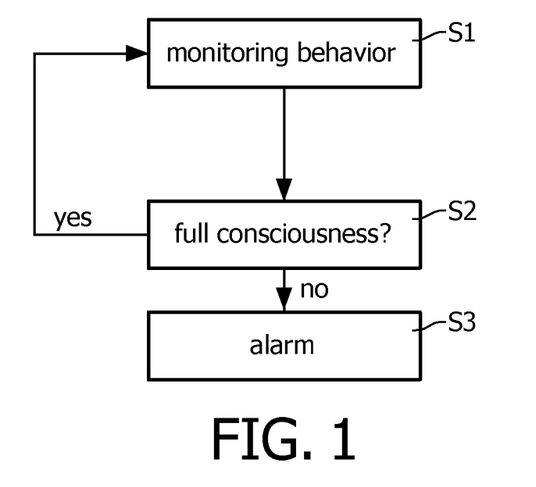
FIG. 1 is a block diagram schematically representing a method for automatically monitoring consciousness of a person and triggering an alarm if the monitored person is not in a state of full consciousness.
Figure 4:
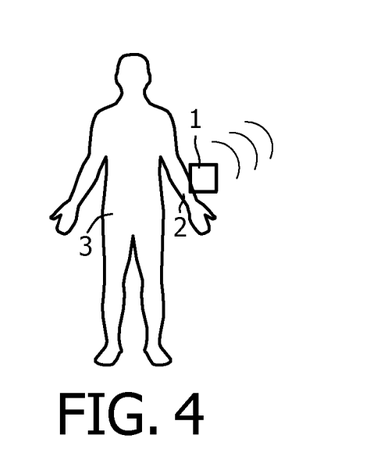
FIG. 4 is a schematic illustration of a monitoring and alarming device in use.

A first embodiment of the present invention will now be described with reference to FIGS. 1, 4, and 5.

The monitoring and alarming device 1 according to the first embodiment is formed by a portable device to be attached to the wrist 2 of a person 3 which can e.g. be a patient in a hospital. The monitoring and alarming device 1 according to the first embodiment comprises only one sensor 4 which is formed by a movement sensor adapted for sensing movement of the body part to which the monitoring and alarming device 1 is attached. The movement sensor can e.g. be formed by a 3-D accelerometer. The sensor 4 is connected (via a connection not shown in the Figures) to a processing unit 5 which is also provided in the monitoring and alarming device 1. The processing unit 5 is adapted to process the signals received from the sensor 4 and deduct information about the performed movements from the signals. Further, specific algorithms are implemented on the processing unit 5 which are adapted to analyze the signal with respect to whether the person 3 to which the monitoring and alarming device 1 is attached to is in a state of full consciousness or not. In this context, the state of full consciousness corresponds to the "Alert" level of the AVPU scale. The algorithm running in the processing unit is adapted to interpret the movement signal and deduce the information with regard to full consciousness or not therefrom as will be explained in the following.

Several different algorithms for distinguishing between a state of full consciousness (alert) and a state of reduced consciousness (non-alert) can be implemented on the processing unit. For example, in the monitoring and alarming device 1 according to the first embodiment the amount of total movement accumulated during a predetermined time period is analyzed and compared to a predetermined threshold value. If the amount is equal to or exceeds the threshold value, it is judged that the patient is in a state of full consciousness (alert). If the amount is lower than the threshold value, it is judged that the patient is not in a state of full consciousness (non-alert). Additionally or alternatively not only the amount of movement can be analyzed but also the pattern of occurring movements can be analyzed for judging whether the patient is in a state of full consciousness or not.

If the analysis in the processing unit 5 results in that the patient is not in the state of full consciousness, output of an alarm to care givers is triggered via a communication unit 6 which is also implemented in the monitoring and alarming device 1. The communication unit 6 is also connected to the processing unit 5 via a suitable connection (not shown). Preferably, the communication unit 6 is adapted to output an alarm via wireless communication but wire-bound communication is also possible. Alternatively, the communication unit 6 could also be provided with a loud speaker or the like for outputting an acoustic alarm signal. Further, the monitoring and alarming device 1 is realized such that the assessment of whether a state of full consciousness is present or not is performed repeatedly, preferably in a fixed interval such as for instance a time interval between 30 minutes and 4 hours, preferably between 1 and 2 hours.

Although it has been described that the analysis is performed in the processing unit which is implemented in the portable device, the analysis can also be performed in a (stationary) patient monitoring unit comprising a processing unit which is located separate from the sensor and receives the signal from the sensor (or pre-processed signal) via a (wireless or wire-bound) connection. In this context it should be noted that the processing unit can also be distributed, e.g. such that a part of the processing unit is located in a portable device, e.g. close to the sensor, and another part of the processing unit is located in a stationary unit. In the case of the processing unit and the sensor being provided separately, preferably a wireless data communication between them is established for reasons of patient comfort. However, wire-bound communication is also possible.

Further, the results of the assessment whether the patient is in a state of full consciousness or not can be stored in an appropriate storage medium (preferably provided with a time-stamp) which can be located in the monitoring and alarming device 1 or in an external device to which the information is transmitted (wirelessly or wire-bound). In this case, the information can be analyzed at later point in time if deemed necessary.

Although it has been described that only one single sensor is provided, it is also possible to provide several motion sensors (e.g. attachable to different body parts) such that movement patterns can be analyzed more reliably. For example a first movement sensor can be attached to the (dominant) wrist and a further movement sensor can be placed on the core body so that, based on the movement directions, changes in body position can be detected and the frequency of change can be used as additional information for assessing the level of consciousness.

Further, although sensors to be attached to body parts have been described above, sensors can also be provided on other objects, such as on the patient bed in a hospital. Such sensors need not be motion sensors. For example, pressure sensors can be attached to the patient bed to detect movement dynamics of a patient. In this case, there is the advantage that patients will likely feel more comfortable as the sensors are not attached to the body.

Since the level of full consciousness (alert level) manifests itself also in other behavioral aspects apart from movement of body parts, other behavioral aspects can additionally or alternatively be monitored. If these other behavioral aspects are additionally monitored this can help increase the sensitivity and specificity of the automatic assessment. For example, the amount of eye movements (i.e. eye opening) can additionally or alternatively be monitored. Eye movements can e.g. be monitored based on electrooculography (EOG) acquired by electrodes placed on the forehead and temples of the patient. As electrodes on the head are often considered obtrusive, a remote sensing solution, such as by a camera as a sensor, can be used instead. Such a camera could for instance be mounted on the patient's personal television apparatus, on furniture located in the patient's vicinity, and the like.

Further, since patients which are in a state of full consciousness are capable of conversing with each other, the amount of conversation can additionally or alternatively be used as an aspect of behavior for assessing whether a state of full consciousness is present or not. The amount of conversation can for instance be measured by a microphone as a (further) sensor. For example, a throat microphone can be attached on the patient's neck.

There are further aspects of behavior of patients which can be used for assessing whether a patient is in a level of full consciousness or not. For example, the amount of the patient's interaction with devices in his/her vicinity, particularly the personal devices dedicated for personal usage such as the personal entertainment devices (TV, radio), personal overhead light, and personal telephone unit, can be used as another behavioral aspect additionally or alternatively. The amount of interaction with such a device can be monitored from registering e.g. the remote control usage (push on zapping button, volume changing button, light switch, and the like) which in this case serves as a (further) sensor.

Although it has been described that only one aspect of the behavior of a patient is monitored (movements measured by a single sensor in the first embodiment), several different aspects of the behavior can of course be monitored and whether a state of full consciousness is present or not can be determined based on the combined information with regard to the different aspects.

The steps of the method according to the first embodiment will briefly be explained again with respect to FIG. 1.

In a step S1, at least one aspect of the behavior of the patient is monitored. It should be noted that exclusively non-invasive monitoring is preferred. In a step S2, the monitored behavior is analyzed as to whether it corresponds to an expected behavior for a state of full consciousness or not. If the result of the analysis in step S2 is "yes", the method steps back to step S1. In this case an appropriate delay can be introduced such that the assessment is performed in regular or irregular intervals. However, if the result of the analysis in step S2 is "no" (i.e. the patient is not in a state of full consciousness), in a step S3 output of an alarm is triggered.

Figure 2:
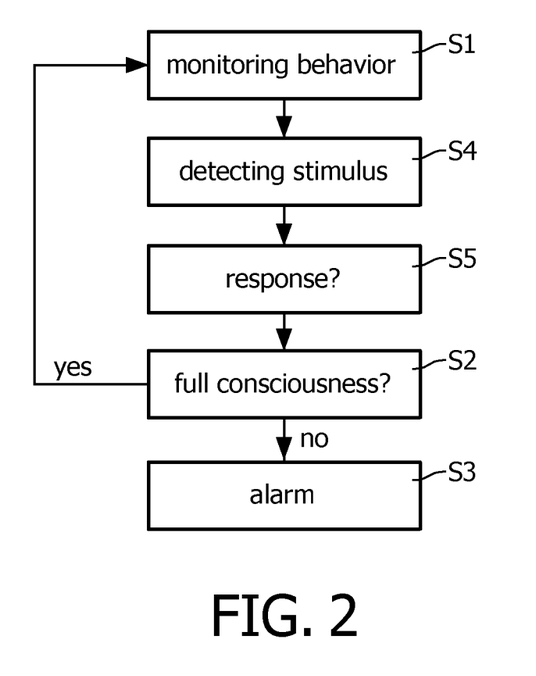
FIG. 2 is a block diagram schematically representing a further method for automatically monitoring consciousness of a person and triggering an alarm if the monitored person is not in a state of full consciousness.

A second embodiment will now be described with respect to FIGS. 2, 4, and 5. The description of the second embodiment will be based on the description of the first embodiment above and only the differences to the first embodiment will be explained. Further, the same reference signs will be used and description of corresponding elements/components will not be repeated. It should be noted that all the alternatives described above with respect to the first embodiment do also apply to the further embodiments and will not be described again.

According to the second embodiment, not only at least one aspect of the behavior of the patient is monitored but also at least one naturally occurring environmental stimulus is detected and the response in the monitored aspect of the behavior to the at least one environmental stimulus is monitored and analyzed. In this context, a naturally occurring environmental stimulus means a stimulus which is not intentionally and artificially generated in order to trigger a response by the patient but is a stimulus which typically occurs in the environment of the patient, such as normal acoustic signals. Although the embodiment will be explained with respect to acoustic signals, there is no restriction to acoustic signals and e.g. light signals/changes, opening of doors, etc. could also be used as environmental stimuli additionally or alternatively.

Figure 5:
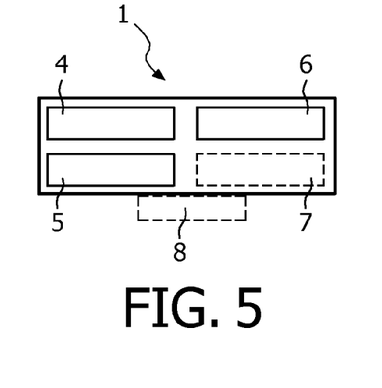
FIG. 5 is a further schematic illustration of the device of FIG. 4.

The monitoring and alarming device 1 according to the second embodiment is further provided with a detection unit 7 for detecting at least one environmental stimulus (shown in dotted lines in FIG. 5). For the case of an acoustic stimulus being the environmental stimulus, the detection unit 7 can e.g. be formed by a microphone for detecting the acoustic signal. The detection unit 7 is connected to the processing unit 5 via a (not shown wireless or wire-bound) connection.

In the example where an acoustic stimulus is exploited, the detection unit 7 is formed by a microphone (or array of microphones) installed in the vicinity of the patient (e.g. in or on the personal telephone unit). According to the embodiment, the sound (acoustic signal) is first sampled and then characterized in the processing unit 5. Preferably, an algorithm for sound characterization is executed which first checks whether the recorded sound corresponds to the patient's voice. This can e.g. be done by correlating the recorded sound with a throat microphone recording. If the recorded acoustic signal contains the patient's voice, the recorded segment is not regarded as a stimulus and hence not further processed. However, in this case, the information can also be used to judge that the patient is in a state of full consciousness. Otherwise, the recorded sound is characterized further, such as for instance by determining the time instance when a sudden change (e.g. in loudness) in the acoustic environment occurs. The response to the identified stimulus in the monitored at least one aspect of behavior (as described with regard to the first embodiment, e.g. body movement, eye movement, voice response, etc.) is then characterized by searching for a change in the monitored at least one aspect of behavior following the time instance when the identified environmental stimulus has occurred. If a change in the monitored at least one aspect of behavior of the patient is detected within a certain period after the occurrence of the stimulus, the patient is considered to respond to the stimulus.

According to the second embodiment, analysis if the monitored behavior of the patient corresponds to an expected behavior for a state of full consciousness is based on both general monitoring of the behavior of the patient and on responses of the patient in the at least one monitored aspect of behavior to at least one naturally occurring environmental stimulus.

The steps of the method for automatically monitoring consciousness of a patient and triggering an alarm if the monitored patient is not in a state of full consciousness according to the second embodiment will now be briefly described again with reference to FIG. 2.

Similarly to the first embodiment, in step S1, at least one aspect of the behavior of a patient is monitored. In a step S4, an environmental stimulus is detected via the detection unit 7 and in a step S5, it is checked whether a (expected) response in the monitored at least one aspect of behavior is found. In step S2, it is judged based on the monitored at least one aspect of the behavior and based on the monitored response to the at least one environmental stimulus whether a state of full consciousness is present or not. If it is judged that full consciousness is given, the method returns to step S1. If it is judged that full consciousness is not given, the method proceeds to step S4 in which output of an alarm is triggered.

Preferably, according to the first and second embodiments, assessment of the consciousness of the patient is performed on a periodical basis, for instance on an hourly basis. Each aspect of behavior which is monitored (in the case of multiple aspects being monitored) is preferably assessed independently based on the respective measured signal in the relevant period. The assessment criterion for judging whether full consciousness is given or not can be the accumulated amount of behavioral aspects, e.g. the accumulated amount of movements of body parts, eye openings, conversions, the number of stimuli the user responded, etc. For each behavioral aspect, the distinction between an expected result for a state of full consciousness and a state of reduced consciousness can be based on threshold values which have been determined before based on field measurements. By applying the thresholds to the corresponding accumulated periodical data, an assessment is obtained for each aspect of the behavior. The combining function which is exploited for combining the results with regard to different aspects of behavior can be for instance an XOR function, or an OR function which will result in judgment of "full consciousness" if at least assessment of one aspect (when considered separately) results in the finding of "full consciousness".

Figure 3:
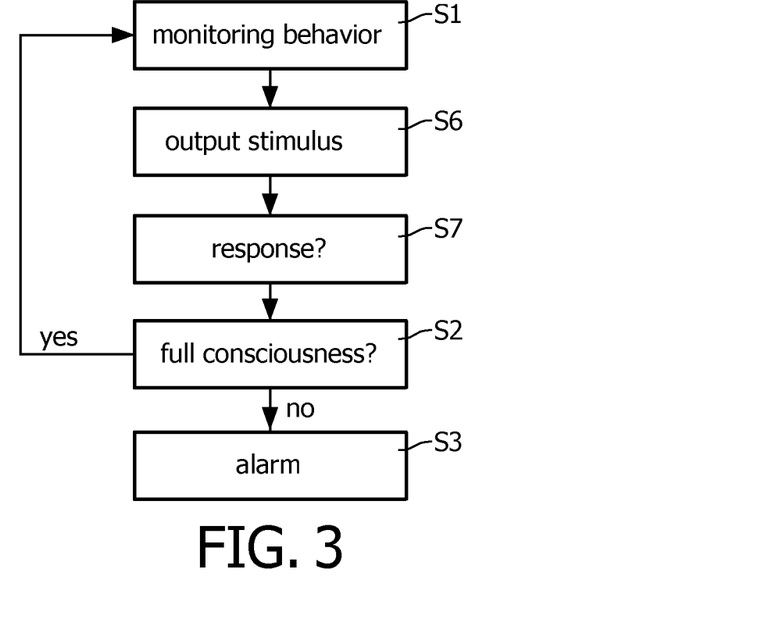
FIG. 3 is a block diagram schematically representing a method for automatically monitoring consciousness of a person and triggering an alarm if the monitored person is not in a state of full consciousness in which a person is subjected to an intentional artificial stimulus.

A third embodiment will now be described with respect to FIGS. 3, 4, and 5. The description of the third embodiment will be based on the description of the first and second embodiments and their modifications and only the differences will be explained. Further, the same reference signs will be used and description of corresponding elements/components will not be repeated. It should be noted that all the alternatives described above with respect to the first and second embodiments do also apply to the third embodiment and will not be described again.

The monitoring and alarming device 1 according to the third embodiment is (additionally to the components described above with respect to the first or second embodiment) provided with at least one stimulation device 8 (shown in dotted lines in FIG. 5) adapted for providing an artificial intentional stimulus to the patient being monitored. The at least one stimulation device 8 is also connected to the processing unit 5 through an appropriate connection (not shown). In the example, the stimulation device 8 is realized by a buzzer integrated into the monitoring and alarming device 1, the buzzer being adapted to issue a small "buzz" to the patient to which the monitoring and alarming device 1 is attached (e.g. in form of a bracelet or the like).

According to the third embodiment, the at least one stimulation device 8 is controlled by the processing unit 5 to provide a small "buzz" to the patient as an intentional artificial stimulus. After the artificial intentional stimulus, the response in the monitored at least one aspect of the behavior of the patient is measured. When the patient is conscious, the stimulus will lead to a reaction of the patient which can be identified as a response in the monitored at least one aspect of behavior. For the particular example in which the monitoring and alarming device 1 is formed by a bracelet to be attached to patient and comprising the buzzer as stimulation device 8 and an accelerometer as sensor 4, the response of the patient will typically be a small movement of the arm which can be sensed by the sensor 4. This particular realization has the advantage that such a response can even be expected at night when the patient is asleep.

According to the third embodiment, the at least one artificial intentional stimulus is activated periodically in intervals between 30 minutes and 4 hours, preferably between 1 hour and 2 hours. It should be noted that issuing the stimulus should not be performed too often in order not to annoy the patient being monitored.

Although in the embodiment the at least one stimulation device 8 is formed by a buzzer, many alternatives exist. For example, the artificial intentional stimulus can also be formed by a vibration, an acoustic signal (such as e.g. a slightly annoying noise such as the sound of a mosquito), a light signal, a challenge or puzzle presented to the patient, etc. A challenge/puzzle presented to the patient could e.g. be an instruction "push the button twice", "push the red and yellow buttons", " add the numbers 1 and 2, and push the button this many times", etc. Correspondingly, the at least one stimulation device 8 can e.g. be formed by one or more light sources for emitting light signals, by one or more loud speakers (or head-phones/ear-phones) for emitting acoustic signals, by a vibrating element, by a patient interface comprising a monitor and input means, and the like. However, it should be noted that the at least one stimulation device 8 is preferably realized such that a non-invasive stimulus is generated as the artificial intentional stimulus. Further, a plurality of similar or different stimulation devices can be provided.

Depending on the kind of artificial intentional stimulus, the reaction of the patient could for example be a movement of a body part or a change in posture, an action such as pushing one or more buttons, entering the answer to a puzzle, a combination of these, and the like. It should be pointed out that the kind of stimulation device should be selected taking into account the monitored at least one behavioral aspect in order to make sure that a detectable response can really be expected.

Similar to the first and second embodiments, in the case that no response (or a wrong/not expected response) to the at least one artificial intentional stimulus is detected in the monitored at least one aspect of behavior, it is judged that the state of full consciousness (alert level) is not present and output of an alarm is triggered such that care personnel can make a full manual assessment of the patient.

Depending on the kind of artificial intentional stimulus, the monitoring and alarming device 1 will have to be adapted such that a naturally unresponsive behavior, e.g. during sleeping periods of the patient, is considered as ineffectual. Further, the monitoring and alarming device 1 can be adapted to work differently during day and night to take into consideration the natural unresponsive behavior during sleep at night. This can be advantageous since waking up patients by providing stimuli during might be undesirable. Furthermore, the monitoring and alarming device 1 may be adapted to ignore a certain number of unresponsive events before alarming. This can be advantageous e.g. in order to avoid false alarms such as those resulting from a nap during the day.

Preferably, the monitoring and alarming device 1 is adapted such that changes in the response time of the patient to a stimulus are tracked over time. A negative trend in response times (i.e. response times becoming longer) can also provide additional health condition information about the patient, e.g. may indicate a decrease in the patient's health condition.

The steps of the method for automatically monitoring consciousness of a person and triggering an alarm if the monitored person is not in a state of full consciousness according to the third embodiment will briefly be explained again with respect to FIG. 3.

In step S1, at least one aspect of the behavior of the person is monitored. In step S6, at least one artificial intentional stimulus is output. In step S7, the response to the at least one artificial intentional stimulus in the monitored behavioral aspect is monitored. In step S2, the monitored behavior is analyzed as to whether it corresponds to an expected behavior for a state of full consciousness or not. If the result of the analysis in step S2 is "yes", the method returns to step S1. In this case an appropriate delay can be introduced such that the assessment is performed in regular or irregular intervals. However, if the result of the analysis in step S2 is "yes" (i.e. the patient is not in a state of full consciousness), in a step S3 output of an alarm is triggered.

Figure 6:
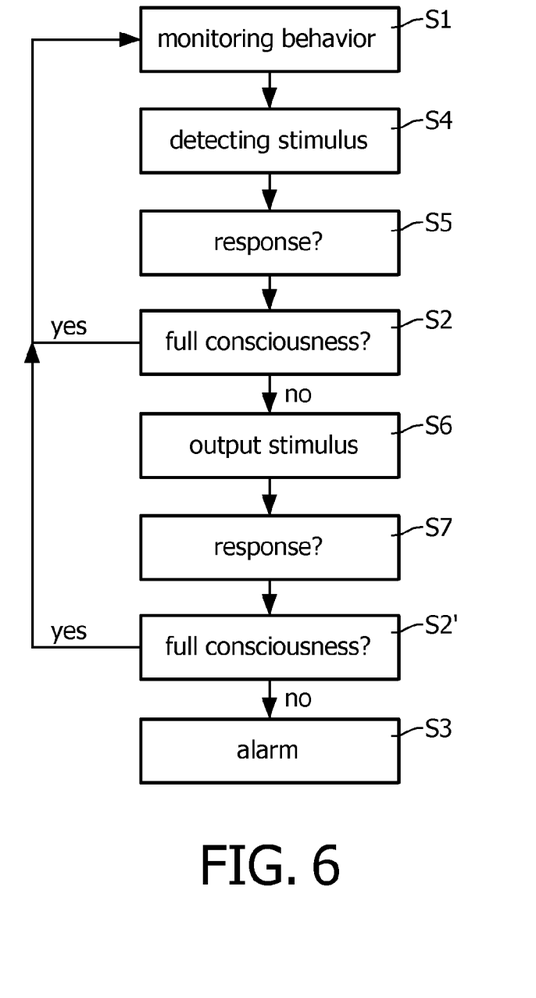
FIG. 6 is a block diagram schematically representing a further method for automatically monitoring consciousness of a person and triggering an alarm if the monitored person is not in a state of full consciousness.

A modification of the third embodiment will be briefly described with respect to FIG. 6. The method according to the modification of the third embodiment is a combination of the second and third embodiments. According to the modification, first the steps S1, S4, S5, and S2 are performed as has been described above with respect to the second embodiment. This means, at least one aspect of the behavior of the patient is monitored, at least one naturally occurring environmental stimulus is detected and the response thereto is monitored. Based on the monitored behavior and the monitored response, in step S2 it is judged whether a state of full consciousness is present or not. In the case that a state of full consciousness is found to be present, the method returns to step S1 as in the second embodiment. However, in the case that it is found that a state different from a state of full consciousness is present ("no" in step S2), steps S6 and S7 of the third embodiment are executed before output of an alarm is triggered. This means, at least one intentional stimulus is output via the at least one stimulation device 8 and the response in the monitored aspect of behavior is analyzed. In a step S2', it is then analyzed whether the response corresponds to an expected response and thus whether a state of full consciousness is present or not. If it is found in step ST (taking into account the response to the intentional stimulus) that a state of full consciousness is present, the method returns to step S1. Otherwise ("no" in step S2'), output of the alarm is triggered.

The modification of the third embodiment has the advantage over the third embodiment that the intentional stimulus is only output if the analysis based on natural stimuli has resulted in that (probably) no full consciousness is given. Thus, the frequency of applying intentional stimuli to the patient can be advantageously reduced such that the problem of potentially annoying the patient and of non-complying patient behavior can be significantly reduced. Further, as compared to the second embodiment, additional redundancy is introduced by application of the at least one intentional stimulus.

Further, although a combination of the second and third embodiments has been described, a combination of the first and third embodiments is also possible. In this case, there are no steps of detecting naturally occurring environmental stimuli and responses thereto but first the steps S1 and S2 of the first embodiment are performed, i.e. monitoring at least one aspect of the behavior and analyzing whether it corresponds to an expected behavior or not. If the step S2 of the first embodiment results in "no", the steps of the third embodiment are performed as in the modification of the third embodiment described immediately above.

Although in the embodiments an alarming and monitoring device 1 has been described which is worn by a person or directly attached to a person, by suitable selection of the sensor 4 (and possibly the stimulation device 8 in the third embodiment) the alarming and monitoring device 1 can also be integrated into the furniture, a personal TV apparatus, a patient identification bracelet, and the like. Many other possibilities exist.

Further, although embodiments have been described in which the monitoring and alarming device 1 is used for monitoring consciousness of patients in general wards of hospitals, the invention shall not be restricted thereto. Besides for applications in a hospital, the described monitoring and alarming device 1 can also be used in other care settings like elderly homes or for home monitoring. Moreover, the monitoring and alarming device 1 can also be used for monitoring alertness of people outside of care settings, e.g. for work forces operating potentially dangerous pieces of equipment or involved in security, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method for automatically monitoring consciousness of a person and triggering an alarm if the monitored person is not in a state of full consciousness; the method comprising the steps:
    monitoring at least one aspect of active behavior of the person;
    detecting at least one environmental stimulus;
    analyzing whether the monitored active behavior of the person in response to detecting the at least one environmental stimulus responds with an expected behavior for a state of full consciousness or not;
    triggering an alarm if the analysis results in that the monitored active behavior does not correspond to the expected behavior.

2. The method according to claim 1, wherein the step of analyzing is performed to discern between exactly two states, namely a state of full consciousness and a state corresponding to not full consciousness.

3. The method according to claim 1, wherein the analysis is responsive to detecting naturally occurring acoustic signals in an environment around the person.

4. The method according to claim 1, wherein in response to the analyzing determining that the monitored behavior does not correspond to the expected behavior for a full state of consciousness:
    subjecting the person to an artificial intentional stimulus;
    analyzing whether the monitored behavior of the person in response to the artificial intensional stimulus corresponds to the expected state of behavior for the state of full consciousness or not and
    wherein the alarm is triggered of the analysis of the monitored behavior of the person to the environmental stimulus and to the artificial intentional stimulus does not correspond to the expected behavior for a full state of consciousness.

5. The method according to claim 1, wherein the person is subjected to at least one artificial intentional stimulus and the response of the person to the at least one intentional stimulus is measured.

6. The method according to claim 5, wherein response times of responses to subsequent stimuli are analyzed and tracked over time.

7. The method according to claim 1, wherein the person is subjected to an artificial intentional stimulus only if the monitored behavior of the person in response to the at least one environmental stimulus does not correspond to an expected behavior for a state of full consciousness.

8. A monitoring and alarming device for automatically monitoring consciousness of a person and outputting an alarm if the monitored person is not in a state of full consciousness, the device comprising:
    at least one sensor configured to sense at least one aspect of the behavior of a person;
    a detection unit configured to detect environmental stimuli;
    a processing unit configured to:
        monitor a signal from the at least one sensor,
        in response to the detection unit detecting an environmental stimulus, analyze whether the sensed behavior indicates
        a response to the detected environmental stimulus and to judge from the sensed behavior whether the person is in a state of full consciousness or not, and
        trigger an alarm in response to judging that the monitored person is not in the state of full consciousness.

9. The monitoring and alarming device according to claim 8, wherein the processing unit is configured to discern between exactly two states, namely a state of full alert consciousness and a state corresponding to less than full consciousness.

10. The monitoring and alarming device according to claim 8, comprising at least one stimulation device configured to provide an artificial intentional stimulus to the person being monitored.

11. The monitoring and alarming device according to claim 8, wherein the processing unit is configured to:
    in response to judging from the sensed behavior that the person is not in the state of full consciousness, provide an artificial intentional stimulus to the person;
    judge from the sensed behavior of the person in response to the artificial intentional stimulus whether the person is in the state of full consciousness; and
    wherein the alarm is triggered in response to judging from the sensed behavior of the person to the environmental stimulus and to the artificial intentional stimulus that the person is not in the full state of consciousness.

12. The monitoring and alarming device according to claim 10, wherein the at least one sensor comprises at least one motion sensor which senses patient movement.

13. The monitoring and alarming device according to claim 12, further including:
    a patient unit configured to be attached to a patient, the patient unit including the at least one motion detector and the stimulation device.

14. The method according to claim 1, wherein the natural environmental stimulus includes one or more of:
    a change in lighting level in an environment of the person;
    a change in acoustic noise level in the environment of the person;

a noise, not caused by the consciousness monitoring, occurring in the environment of the person.

15. The monitoring and alarming device according to claim 8, wherein the natural environmental stimulus includes one or more of:
   a change in lighting level in an environment of the person;
   a change in acoustic noise level in the environment of the person;
   a noise, not caused by the monitoring and alarming device, occurring in the environment of the person.

16. A monitoring and alarming device for automatically monitoring consciousness of a person and outputting an alarm if the monitored person is not in a state of full consciousness, the device comprising:
   a sensor unit configured to sense at least one aspect of the behavior of a person;
   at least one of:
      a detector configured to detect an occurrence of a natural environmental stimulus, and
      a stimulation unit configured to apply an artificial intentional stimulus to the person;
   a computer processor configured to:
      analyze the sensed aspect of the behavior and judge whether the person is in a state of full consciousness,
      in response to judging that the person is not in a state of full consciousness, at least one of (i) receive an input from the detector that the natural, environmental stimulus has been received and (ii) control the stimulation unit to apply the artificial stimulus to the person,
      analyze the behavior of the person in response to the stimulus and judge whether the person is in the state of full consciousness, and
      in response to judging from the analysis of the response to the stimulus that the person is not in the state of full consciousness, triggering an alarm.

17. The monitoring and alarming unit according to claim 16, wherein the sensor includes a microphone and the computer processor is configured to determine that the person is in the state of full consciousness in response to the microphone hearing the voice of the person.

18. The monitoring and alarming unit according to claim 16, wherein the natural environmental stimulus includes one or more of:
   a change in lighting level in an environment of the person;
   a change in acoustic noise level in the environment of the person;
   a noise, not caused by the monitoring and alarming device, occurring in the environment of the person.

19. The monitoring and alarming unit according to claim 14, further including both the detector and the stimulation unit and wherein the processor is further configured to:
   in response to judging that the person is not in the state of full consciousness after a preselected plural number of natural environmental stimuli, controlling the stimulation unit to apply the artificial intentional stimulus; and
   in response to judging from the analyzed response to the artificial intentional stimulus that the person is not in the state of full consciousness, triggering an alarm to summon a medical professional to evaluate the state of consciousness of the person.

20. The monitoring and alarming device according to claim 16, wherein the sensor unit is further configured to sense heart rate, blood pressure, respiration rate, and temperature such that the monitoring and alarming device monitors the heart rate, the blood pressure, the respiration rate, the temperature, and the state of consciousness of the person.

* * * * *